(12) United States Patent
Cruise et al.

(10) Patent No.: US 8,231,890 B2
(45) Date of Patent: Jul. 31, 2012

(54) HYDROGELS THAT UNDERGO VOLUMETRIC EXPANSION IN RESPONSE TO CHANGES IN THEIR ENVIRONMENT AND THEIR METHODS OF MANUFACTURE AND USE

(75) Inventors: Gregory M. Cruise, Rancho Santa Margarita, CA (US); Michael J. Constant, Mission Viejo, CA (US)

(73) Assignee: MicroVention, Inc., Tustin, CA (US)

( * ) Notice: Subject to any disclaimer, the term of this patent is extended or adjusted under 35 U.S.C. 154(b) by 1598 days.

(21) Appl. No.: 11/090,806

(22) Filed: Mar. 24, 2005

(65) Prior Publication Data
US 2005/0196426 A1 Sep. 8, 2005

Related U.S. Application Data

(63) Continuation of application No. 09/804,935, filed on Mar. 13, 2001, now Pat. No. 6,878,384.

(51) Int. Cl.
*A61F 2/02* (2006.01)
(52) U.S. Cl. ........................................... 424/424
(58) Field of Classification Search .................. None
See application file for complete search history.

(56) References Cited

U.S. PATENT DOCUMENTS

| | | | |
|---|---|---|---|
| 5,415,864 A | 5/1995 | Kopecek et al. | |
| 5,447,727 A * | 9/1995 | Graham | 424/487 |
| 5,863,551 A | 1/1999 | Woerly et al. | |
| 6,103,865 A | 8/2000 | Bae et al. | |
| 6,224,893 B1 * | 5/2001 | Langer et al. | 424/423 |
| 6,333,109 B1 * | 12/2001 | Harada et al. | 428/402 |
| 6,335,028 B1 * | 1/2002 | Vogel et al. | 424/422 |
| 2003/0014075 A1 * | 1/2003 | Rosenbluth et al. | 606/213 |

FOREIGN PATENT DOCUMENTS

| | | |
|---|---|---|
| EP | 1 024 176 | 8/2000 |
| WO | 91/04732 | 4/1991 |

OTHER PUBLICATIONS

Hoffman, Allan S., "Intelligent Polymers in Medicine and Biotecg\hnology", pp. 458-467, Artif Organs, vol. 19, No. 5, 1995.

(Continued)

*Primary Examiner* — Carlos Azpuru
(74) *Attorney, Agent, or Firm* — K&L Gates LLP; Louis C. Cullman; Brian J. Novak

(57) ABSTRACT

Hydrogels that expand volumetrically in response to a change in their environment (e.g., a change in pH or temperature) and their methods of manufacture and use. Generally, the hydrogels are prepared by forming a liquid reaction mixture that contains a) monomer(s) and/or polymer(s) at least portion(s) of which are sensitive to environmental changes (e.g., changes in pH or temperature), b) a crosslinker and c) a polymerization initiator. If desired, a porosigen may be incorporated into the liquid reaction mixture to create pores. After the hydrogel is formed, the porosigen is removed to create pores in the hydrogel. The hydrogel may also be treated to cause it to assume a non-expanded volume in which it remains until a change in its environment causes it to expand. These hydrogels may be prepared in many forms including pellets, filaments, and particles. Biomedical uses of these hydrogels include applications wherein the hydrogel is implanted in the body of a patient and an environmental condition at the implantation site causes the hydrogel to expand in situ.

26 Claims, 2 Drawing Sheets

OTHER PUBLICATIONS

Akala, Emmanuel O., Kopeckova, Pavia, and Kopecek, Jindrich, "Novel pH-sensitive hydrogels with adjustable swelling kinetics", pp. 1037-1047, Biomaterials 19 (1998).

Galaev, Igor Y. and Mattlasson, Bo, "Smart Polymers and what they could do in biotechnology and medicine", pp. 335-340, Tibtech Aug. 1999 vol. 17.

Canadian Office Action for Application No. 2,439,925 mailed Nov. 21, 2011.

European Search Report for Application No. 10188595.2 mailed Aug. 4, 2011.

Chen, Guohua and Hoffman, Allan S., Graft copolymers that exhibit temperature-induced phase transitions over a wide range of pH, Nov. 14, 1994, Nature, vol. 373, pp. 49-52.

Klier, J., Scranton, A.B., and Peppas, N.A., Self-Associating Networks of Poly(methacrylic acid-g-ethylene glycol), Mar. 26, 1990, Macromolecules 1990, vol. 23, pp. 4944-4949.

Oxlye, H.R., Corkill, P.H., Fitton, J.H. and Tighe, B.J., Macroporous hydrogels for biomedical applications: methodology and morphology, 1993, Biomaterials, vol. 14, No. 14, pp. 1064-1072.

Akala et al., *Novel pH-sensitive hydrogels with adjustable swelling kinetics*, Biomaterials 1998, vol. 19, pp. 1037-1047.

Chen et al., *Graft copolymers that exhibit temperature-induced phase transitions over a wide range of pH*, Nature, Nov. 14, 1994, vol. 373, pp. 49-52.

Galaev et al., *Smart Polymers and what they could do in biotechnology and medicine*, Tibtech, Aug. 1999, vol. 17, pp. 335-340.

Hoffman, Allan S., *Intelligent Polymers in Medicine and Biotechnology*, Artif Organs 1995, vol. 19, No. 5, pp. 458-467.

Klier et al., *Self-Associating Networks of Poly(methacrylic acid-g-ethylene glycol)*, Macromolecules, Mar. 26, 1990, vol. 23, pp. 4944-4949.

Oxlye et al., *Macroporous hydrogels for biomedical applications: methodology and morphology*, Biomaterials 1993, vol. 14, No. 14, pp. 1064-1072.

\* cited by examiner

HYDROGELS THAT UNDERGO VOLUMETRIC EXPANSION IN RESPONSE TO CHANGES IN THEIR ENVIRONMENT AND THEIR METHODS OF MANUFACTURE AND USE

RELATED APPLICATION

This is a continuation of application Ser. No. 09/804,935 filed on Mar. 13, 2001, now issued as U.S. Pat. No. 6,878,384 on Apr. 12, 2005.

FIELD OF THE INVENTION

The present invention relates generally to certain hydrogel compositions, methods of manufacturing such hydrogel compositions and methods of using such hydrogel compositions. More particularly, the present invention relates to hydrogels that exhibit controlled rates of expansion in response to changes in their environment, the methods by which such hydrogels may be prepared and methods of using such hydrogels in biomedical applications (e.g., the treatment of aneurysms, fistulae, arterio-venous malformations, and for embolization or occlusion of blood vessels or other luminal anatomical structures).

BACKGROUND OF THE INVENTION

Generally, the term "hydrogel" refers generally to a polymeric material that is capable swelling in water. The swelling of a hydrogel in water results from diffusion of water through the glassy polymer causing disentanglement of polymer chains and subsequent swelling of the polymer network. Typically, hydrogels of the prior art have been prepared by the crosslinking of monomers and/or polymers by radiation, heat, reduction-oxidation, or nucleophilic attack. Examples of the crosslinking of ethylenically unsaturated monomers include the preparation of contact lenses from 2-hydroxyethyl methacrylate and the preparation of absorbent articles from acrylic acid. Examples of crosslinking of polymers include wound dressings by crosslinking aqueous solutions of hydrophilic polymers using ionizing radiation and surgical sealants by crosslinking aqueous solutions of hydrophilic polymers modified with ethylenically unsaturated moieties.

In or about 1968, Krauch and Sanner described a method of polymerizing monomers around a crystalline matrix and subsequently removing the crystalline matrix to produce an interconnected porous polymer network. Since that time, porous hydrogels have been prepared using salt, sucrose, and ice crystals as the porosigen. These porous hydrogels of the prior art have been used as membranes for affinity chromatography and as tissue engineering substrates wherein tissues are intended to ingrow into the porous hydrogel network. Examples of these porous hydrogels are found in U.S. Pat. Nos. 6,005,161 (Brekke, et al.) entitled Method And Device For Reconstruction of Articular Cartilage, 5,863,551 (Woerly) entitled Implantable Polymer Hydrogel For Therapeutic Uses and 5,750,585 (Park et al.) entitled Super Absorbent Hydrogel Foams.

The prior art has also included certain hydrogels that undergo a volume change in response to external stimuli such as changes in the solvent composition, pH, electric field, ionic strength, and temperature. The hydrogel's response to the various stimuli is due to the judicious selection of the monomer units. For example, if temperature sensitivity is desired, N-isopropyl acrylamide is frequently used. If pH sensitivity is desired, a monomer with an amine group or a carboxylic acid is frequently used. Stimuli responsive hydrogels have primarily been used as controlled drug delivery vehicles. Examples of these stimuli-responsive hydrogels are found in U.S. Pat. Nos. 6,103,865 (Rae, et al) entitled pH-Sensitive Polymer Containing Sulfonamide And Its Synthesis Method, 5,226,902 (Bae et al.) entitled Pulsatile Drug Delivery Device Using Stimuli Sensitive Hydrogel and 5,415,864 (Kopeck, et al.) entitled Colonic-Targeted Oral Drug-Dosage Forms Based On Crosslinked Hydrogels Containing Azobonds And Exhibiting pH-Dependent Swelling.

Despite these advances in the capabilities of the hydrogel material, a hydrogel material that permits cellular ingrowth and has controlled rate of expansion optimized for delivery through a microcatheter or catheter without the need for a non-aqueous solvent or a coating has not been developed. Accordingly, there remains a need in the art for the development of such a hydrogel useable in various applications, including, but not limited to, medical implant applications wherein the hydrogel is used as or in conjunction with aneurysms, fistulae, arterio-venous malformations, and vessel occlusions.

SUMMARY OF THE INVENTION

The present invention provides hydrogels that undergo controlled volumetric expansion in response to changes in their environment, such as changes in pH or temperature (i.e., they are "stimulus-expandable"). In one embodiment, the hydrogels are sufficiently porous to permit cellular ingrowth. The hydrogels of the present invention are prepared by forming a liquid reaction mixture that contains a) monomer(s) and/or polymer(s) at least portion(s) of which are sensitive to environmental changes (e.g., changes in pH or temperature), b) a crosslinker and c) a polymerization initiator. If desired, a porosigen, (e.g., sodium chloride, ice crystals, and sucrose) may be incorporated into the liquid reaction mixture. Porosity is formed by the subsequent removal of the porosigen from the resultant solid hydrogel (e.g, by repeated washing). Typically, a solvent will also be used to dissolve solid monomer(s) and/or polymers. However, in cases where only liquid monomers are used, there may be no need for inclusion of a solvent. Generally, the controlled rate of expansion of the present invention is imparted through the incorporation of ethylenically unsaturated monomers with ionizable functional groups, (e.g. amines, carboxylic acids). For example, if acrylic acid is incorporated into the crosslinked network, the hydrogel is incubated in a low pH solution to protonate the carboxylic acids. After the excess low pH solution has been rinsed away and the hydrogel dried, the hydrogel can be introduced through a microcatheter filled with saline at physiological pH or blood. The hydrogel cannot expand until the carboxylic acid groups deprotonate. Conversely, if an amine containing monomer is incorporated into the crosslinked network, the hydrogel is incubated in a high pH solution to deprotonate amines. After the excess high pH solution has been rinsed away and the hydrogel dried, the hydrogel can be introduced through a microcatheter filled with saline at physiological pH or blood. The hydrogel cannot expand until the amine groups protonate.

Optionally, a stimulus-expandable hydrogel material of the present invention may be rendered radiopaque for visualization under radiographic imaging. The incorporation of radiopaque particles (e.g., tantalum, gold, platinum, etc.) into the liquid reaction mixture would impart radiopacity to the entire hydrogel. Alternatively, a radiopaque monomer may be incorporated into the liquid reaction mixture to impart radiopacity to the entire hydrogel.

In accordance with this invention, there are provided methods for treating various diseases, conditions, malformations, or disorders of human or veterinary patients by implanting (e.g. injecting, instilling, implanting surgically or otherwise, introducing through a cannula, catheter, microcatheter, needle or other introduction device or otherwise placing) a stimulus-expandable hydrogel material of the present invention that occupies a first volume into an implantation site within the body whereby the conditions (e.g., pH, temperature) at the implantation site cause the hydrogel to expand to a second volume larger than the first volume. Specifically, the hydrogels of the present invention may be implanted subcutaneously, in a wound, in a tumor or blood vessels that supply blood to the tumor, in an organ, in an aberrant blood vessel or vascular structure, in a space located between or among tissues or anatomical structures or within a surgically created pocket or space. In this manner, the hydrogels that have controllable rates of expansion of the present invention are useable for the treatment of aneurysms, fistulae, arteriovenous malformations, vessel occlusions, and other medical applications.

Further aspects of this invention will be come apparent to those of skill in the art upon reading of the detailed description of exemplary embodiments set forth herebelow.

DETAILED DESCRIPTION OF THE INVENTION

Figure 1:
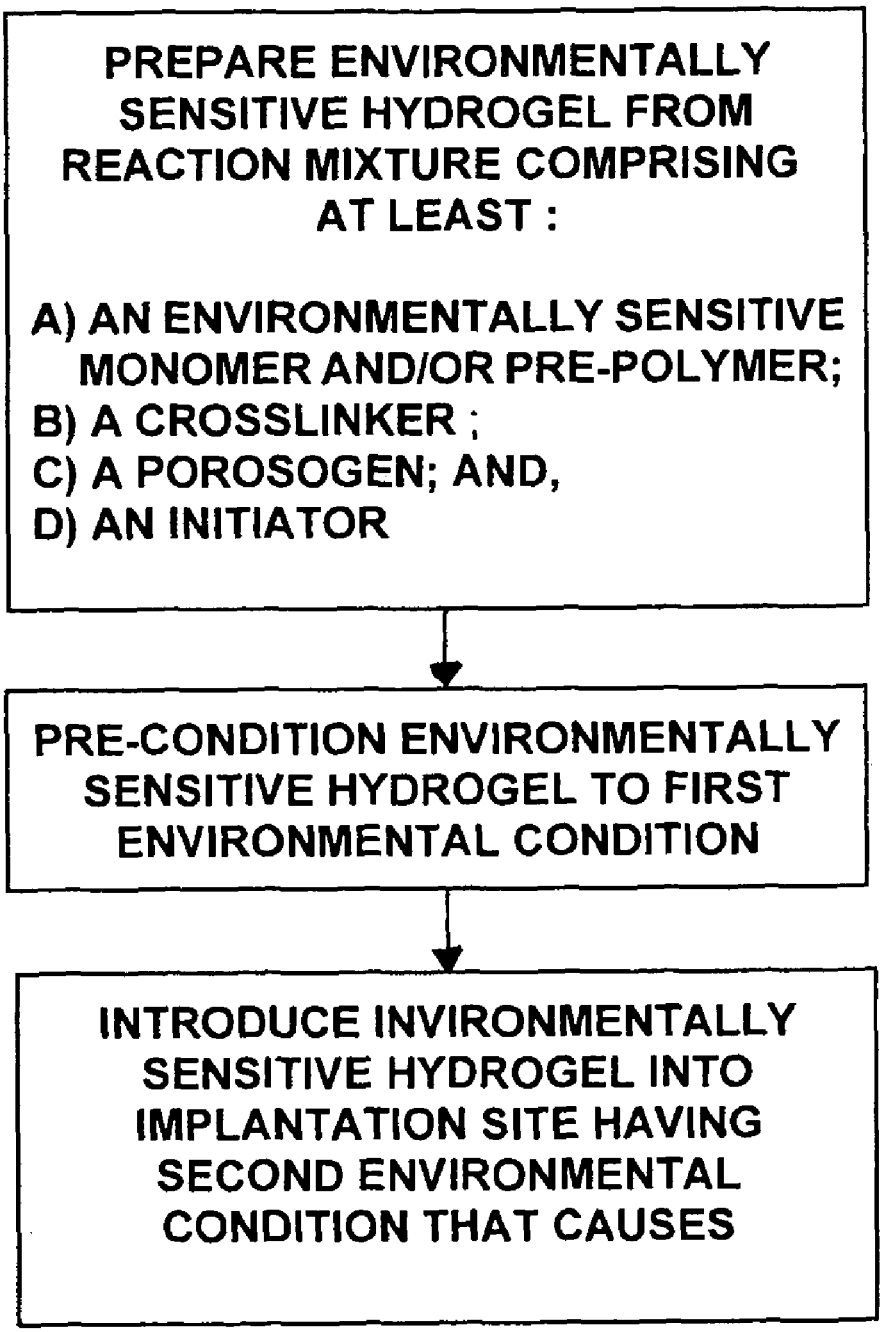
FIG. 1 is a flow diagram showing the general method by which environmentally-responsive expandable hydrogels of the present invention are prepared.

The following detailed description and examples are provided for the limited purpose of illustrating exemplary embodiments of the invention and not for the purpose of exhaustively describing all possible embodiments of the invention.

A. Preferred Method for Preparing pH-Responsive Expandable Hydrogels from Monomer Solutions The following is a description of one method for preparing pH-responsive expandable hydrogels according to the present invention.

Selection and Addition of the Monomers

In this embodiment, the monomer solution is comprised of ethylenically unsaturated monomers, ethylenically unsaturated crosslinker, the porosigen, and the solvent. At least a portion, preferably 10%-50% of the monomers, more preferably 10%-30% of the monomers, of the monomers selected must be pH sensitive. The preferred pH sensitive monomer is acrylic acid. Methacrylic acid and derivatives of both acids will also impart pH sensitivity. Since the mechanical properties of hydrogels prepared exclusively with these acids are poor, a monomer to provide additional mechanical properties should be selected. A preferred monomer for conferrance of mechanical properties is acrylamide, which may be used in combination with one or more of the above-mentioned pH sensitive monomers to impart additional compressive strength or other mechanical properties. Preferred concentrations of the monomers in the solvent range from 20% w/w to 30% w/w.

Selection and Addition of the Crosslinker(s):

The crosslinker can be any multifunctional ethylenically unsaturated compound. N,N'-methylenebisacrylamide is the preferred crosslinker. If biodegradation of the hydrogel material is desired, a biodegradable crosslinker should be selected. Preferred concentrations of the crosslinker in the solvent are less than 1% w/w, more preferably less than 0.1% w/w.

Selection and Addition of the Porosigen(s):

The porosity of the hydrogel material is imparted due to a supersaturated suspension of a porosigen in the monomer solution. A porosigen that is not soluble in the monomer solution, but is soluble in the washing solution can also be used. Sodium chloride is the preferred porosigen, but potassium chloride, ice, sucrose, and sodium bicarbonate can also be used. It is preferred to control the particle size of the porosigen to less than 25 microns, more preferably less than 10 microns. The small particle sizes aid the suspension of the porosigen in the solvent. Preferred concentrations of the porosigen range from 5% w/w to 50% w/w, more preferably 10% w/w to 20% w/w, in the monomer solution. Alternatively, the porosigen can omitted and a non-porous hydrogel can be fabricated.

Selection and Addition of Solvent (if Required):

The solvent, if necessary, is selected based on the solubilities of the monomers, crosslinker, and porosigen. If a liquid monomer (e.g. 2-hydroxyethyl methacrylate) is used, a solvent is not necessary. A preferred solvent is water, however ethyl alcohol can also be used. Preferred concentrations of the solvent range from 20% w/w to 80% w/w, more preferably 50% w/w to 80% w/w.

The crosslink density substantially affects the mechanical properties of these hydrogel materials. The crosslink density (and hence the mechanical properties) can best be manipulated through changes in the monomer concentration, crosslinker concentration, and solvent concentration.

Selection and Addition of Initiator(s) to Cause Crosslinking of the Monomer Solution The crosslinking of the monomer can be achieved through reduction-oxidation, radiation, and heat. Radiation crosslinking of the monomer solution can be achieved with ultraviolet light and visible light with suitable initiators or ionizing radiation (e.g. electron beam or gamma ray) without initiators. A preferred type of crosslinking initiator is one that acts via reduction-oxidation. Specific examples of such red/ox initiators that may be used in this embodiment of the invention are ammonium persulfate and N,N,N',N'-tetramethylethylenediamine.

Washing to Remove Porosigen(s) and any Excess Monomer:

After the polymerization is complete, the hydrogel is washed with water, alcohol or other suitable washing solution(s) to remove the porosigen(s), any unreacted, residual monomer(s) and any unincorporated oligomers. Preferably this is accomplished by initially washing the hydrogel in distilled water.

Treatment of the Hydrogel to Control of the Expansion Rate of the Hydrogel

As discussed above, the control of the expansion rate of the hydrogel is achieved through the protonation/deprotonation of ionizable functional groups present on the hydrogel network. Once the hydrogel has been prepared and the excess monomer and porosigen have been washed away, the steps to control the rate of expansion can be performed.

In embodiments where pH sensitive monomers with carboxylic acid groups have been incorporated into the hydrogel network, the hydrogel is incubated in a low pH solution. The free protons in the solution protonate the carboxylic acid groups on the hydrogel network. The duration and temperature of the incubation and the pH of the solution influence the amount of control on the expansion rate. Generally, the duration and temperature of the incubation are directly proportional to the amount of expansion control, while the solution pH is inversely proportional. It has been determined by applicant that the water content of the treating solution also affects the expansion control. In this regard, the hydrogel is able to expand more in the treating solution and it is presumed that an increased number of carboxylic acid groups are available for protonation. An optimization of water content and pH is required for maximum control on the expansion rate. After the incubation is concluded, the excess treating solution is washed away and the hydrogel material is dried. We have observed that the hydrogel treated with the low pH solution dries down to a smaller dimension than the untreated hydrogel. This is a desired effect since delivery of these hydrogel materials through a microcatheter is desired.

If pH sensitive monomers with amine groups were incorporated into the hydrogel network, the hydrogel is incubated in a high pH solution. Deprotonation occurs on the amine groups of the hydrogel network at high pH. The duration and temperature of the incubation, and the pH of the solution, influence the amount of control on the expansion rate. Generally, the duration, temperature, and solution pH of the incubation are directly proportional to the amount of expansion control. After the incubation is concluded, the excess treating solution is washed away and the hydrogel material is dried.

Example 1

Method for Preparing Pellets of pH-Responsive Expandable Hydrogen

Figure 2:
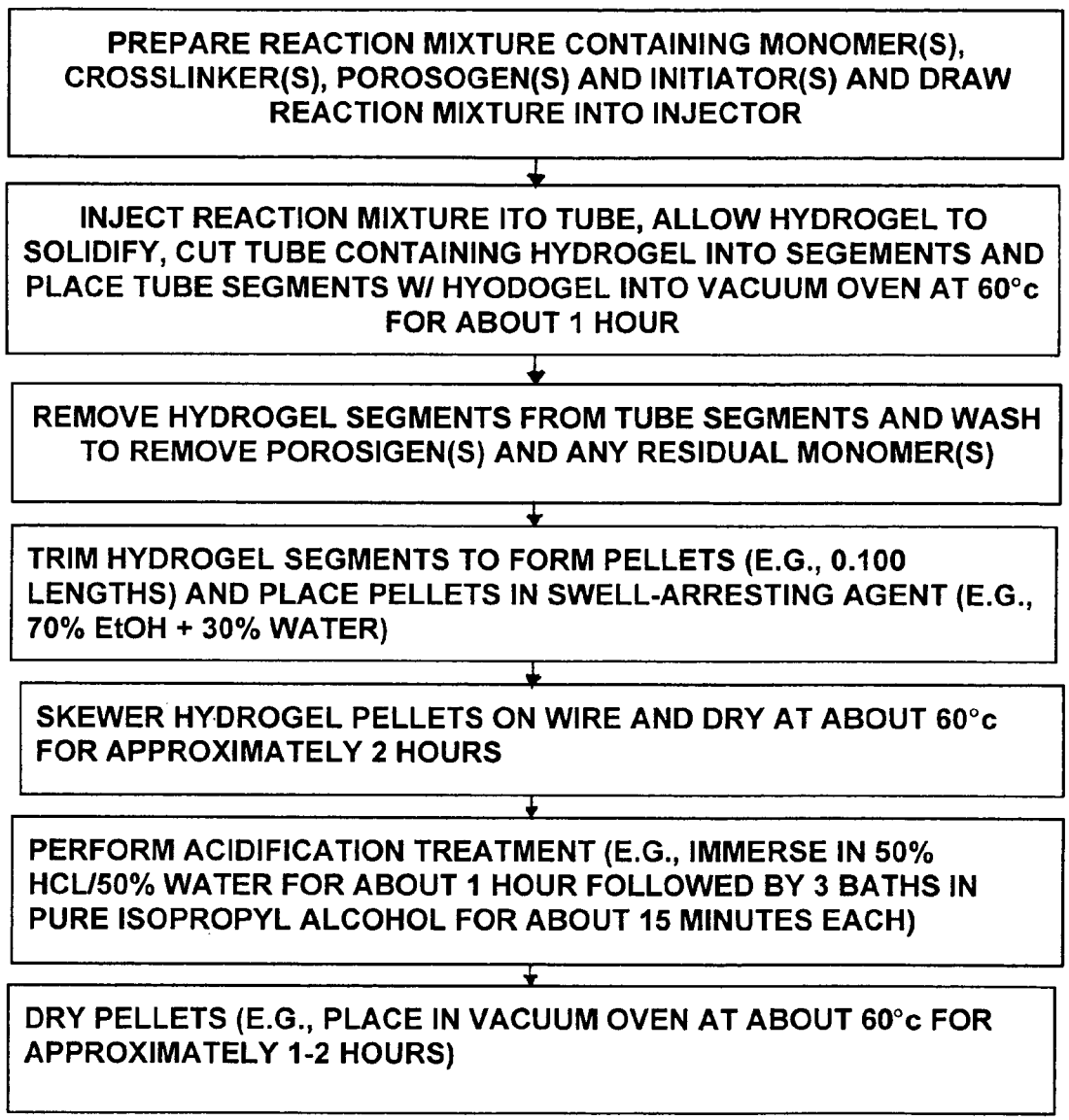
FIG. 2 is a flow diagram showing a specific method by which pH-responsive expandable hydrogel pellets of the present invention may be prepared.

The hydrogel materials of this invention may be produced and used in various forms and configurations, such as sheets, wads, balls, pellets, filaments, etc. FIG. 2 shows a specific example of a presently preferred procedure that may be used to produce a pH-responsive expandable hydrogel of this invention in the from of solid pellets. In this procedure, the initial reaction mixture containing the ethylenically unsaturated monomer(s), ethylenically unsaturated crosslinker(s), porosigen(s) and any solvent(s) is mixed in a suitable vessel. The initiator(s) is/are then added to the mixture and the reaction mixture, while still in liquid form, is further mixed and drawn into a syringe or other suitable injector device. A tube (e.g., a polyethylene tube having an inner diameter of 0.015-0.100 inch and preferably 0.025 inch (id) tubing for the formation of small pellets useable in cerebral or other vascular applications) is attached to the syringe or injector device and the reaction mixture is injected into the tube where it polymerizes. After the hydrogel is fully polymerized within the tube, the tube with the hydrogel contained therein is then cut into individual pieces of desired length (e.g., 2 inch segments). The pieces of hydrogel are then removed from the lumen of each segment of the tube and are placed in a series of rinsing baths to wash out the porosigen(s) and any residual monomer(s). These rinsing baths may be as follows:

| Rinse Bath 1 | distilled water at 55° C. for 10-12 hours |
| Rinse Bath 2 | distilled water at 55° C. for at least 2 hours |
| Rinse Bath 3 | distilled water at 55° C. for at least 2 hours |

During exposure to water in these baths, the hydrogel segments may swell. To arrest the swelling of these hydrogel pellets, they are placed in a swell-arresting solution that displaces at least some of the water from the hydrogel. This swell-arresting solution may be alcohol, an alcohol/water solution that contains sufficient alcohol to control the swelling, acetone, or other suitable non-aqueous dehydrating agent. In the particular example shown in FIG. 2, the previously rinsed hydrogel segments are placed in swell-arresting bath as follows:

| Swell-Arresting Bath | 70% water and 30% ethanol at 55 C. for at least 2 hours |

After removal from the swell-arresting solution, the cylindrical segments of hydrogel may be cut into smaller sections (e.g., 0.100 inch length sections). These individual sections may then be skewered onto a platinum coil and/or platinum wire along the ling axis of the cylindrical hydrogel sections. After skewering, the sections are dried at 55 C under vacuum for at least 2 hours. The hydrogel sections are then subjected to an acidifying treatment, preferably by immersing them in an acidifying solution such as 50% hydrochloric acid:50% water at 37 C for approximately 70 hours. The excess acidifying solution is then washed off. This may be accomplished by placing the hydrogel sections in a series of baths as follows:

| Acidifying Treatment Bath 1 | 70% isopropyl Alcohol and 30% water for about 5 minutes |
| Acidifying Treatment Bath 2 | Pure isopropyl alcohol for about 15 minutes |
| Acidifying Treatment Bath 3 | Pure isopropyl alcohol for about 15 minutes |
| Acidifying Treatment Bath 4 | Pure isopropyl alcohol for about 15 minutes |

After completion of the acidifying treatment (e.g., after removal from the Acidifying Treatment Bath 4) the hydrogel segments (i.e., "pellets") are dried in a vacuum oven at approximately 60 C for about 1 to 2 hours. This completes the preparation of the pellets. These pellets will expand substantially when they come into contact with a liquid (e.g., blood) at physiological pH (i.e., a pH of approximately 7.4).

The following Examples 2-4 are directed to some of the many biomedical applications of the porous hydrogels having controlled rates of expansion, as described herein. Although these examples are limited to a few biomedical applications wherein the hydrogels are implanted into the body of a human or veterinary patient, it will be appreciated that the hydrogel materials of the present invention may be used for many other medical and non-medical applications in addition to the specific examples set forth herebelow.

Example 2

Embolization of Aneurysms

For the embolization of aneurysms, 1.52 g (0.021 moles) acrylamide, 0.87 g (0.009 moles) sodium acrylate, 0.005 g (0.00003 moles) N,N-methylenebisacrylamide, 7.95 g water, and 4.5 g sodium chloride (<10 micron particle size) are added to an amber jar. The initiators, 53 microliters of N,N,N',N'-tetramethylethylenediamine and 65 microliters of 20% w/w ammonium persulfate in water, are added and the solution is aspirated into a 3-cc syringe. The solution is then injected into 0.025" ID tubing and allowed to polymerize for 2 hours. The tubing is cut into 2-inch sections and dried in a vacuum oven. The dried hydrogel is removed from the tubing using a mandrel. The polymerized hydrogel is washed 3 times in distilled water for 10-12 hours, at least 2 hours and at least 2 hours, respectively, to remove porosigen, any unreacted monomer and any unincorporated monomers. The hydrogel is cut into sections ("pellets") of approximately 0.100 inch length and skewered with a platinum coil/wire assembly. These pellets are then dehydrated in alcohol and dried under vacuum at approximately 55 C for about 2 hours.

The dried pellets are then placed in 50% hydrochloric acid/50% water and incubated for about 70 hours at 37 C. After the incubation, the excess hydrochloric acid solution is rinsed off of the pellets with consecutive rinses of a) 70% isopropyl alcohol:30% water for about 5 minutes, b) 100% isopropyl alcohol for about 15 minutes, c) 100% isopropyl for about 15 minutes and d) 100% isopropyl alcohol for about 15 minutes. The hydrogel pellets are then dried under vacuum at 55 C for at least 2 hours.

The treated, dried hydrogel pellets prepared using this procedure have diameters that are suitable for delivery through a 0.014 inch or 0.018 inch (ID) microcatheter that is filled with saline or blood. The material can be injected through the microcatheter with flow (e.g., by mixing the hydrogel pellets or particles with a liquid carrier and injecting or infusing the liquid carrier/hydrogel mixture through a cannula or catheter to the implantation site) with or attached to a detachable delivery system (a wire or tether to which the hydrogel is attached, such wire or tether being advanceable through the lumen of a catheter and into the desired implantation site, whereat the hydrogel will typically remain attached to the wire or tether until the operator causes it to become detached or until some environment condition at the implantation site causes the attachment between the wire/tether and hydrogel to degrade, breakdown or otherwise sever). If a detachable delivery system is utilized, the hydrogel pellets can typically be advanced out of and retracted into the microcatheter (repeatedly if necessary) so long as the wire or teather remains attached and for at least 15 minutes before substantial swelling of the hydrogel occurs. The hydrogel pellets become fully swollen (to diameters of about 0.035 inch) after approximately one hour at physiological pH (about 7.4)

Example 3

Embolization of Arterio-Venous Malformations

To make material suitable for the embolization of arterio-venous malformations, 1.52 g (0.021 moles) acrylamide, 0.87 g (0.009 moles) sodium acrylate, 0.005 g (0.00003 moles) N,N-methylenebisacrylamide, 7.95 g water, and 4.5 g sodium chloride (<10 micron particle size) are added to an amber jar. The initiators, 53 microliters of N,N,N',N'-tetramethylethylenediamine and 65 microliters of 20% w/w ammonium persulfate in water, are added and the solution is aspirated into a 3-cc syringe. The solution is allowed to polymerize inside the syringe for 2 hours. The syringe is removed using a razor blade and the hydrogel is dried in the vacuum oven.

The dried hydrogel is washed three times in distilled water for 10-12 hours, 2 hours and 2 hours, respectively, to remove the porosigen, any unreacted monomer and any unincorporated oligomer(s). The hydrogel is then dehydrated in ethanol and dried under vacuum at about 55 C for approximately 2 hours. The dried hydrogel is the macerated into particles of desired size, typically 100-900 microns in diameter. The dried particles are then incubated in an acidification solution of 50% hydrochloric acid:50% water for approximately 22 hours at about 37 C. After the incubation, the excess hydrochloric acid solution is rinsed off of the pellets with consecutive rinses of a) 70% isopropyl alcohol:30% water for about 5 minutes, b) 100% isopropyl alcohol for about 15 minutes, c) 100% isopropyl for about 15 minutes and d) 100% isopropyl alcohol for about 15 minutes. The treated hydrogel particles are then dried under vacuum at about 55 C for approximately 2 hours. The treated, dried hydrogel particles prepared by this procedure have diameters that are suitable for embolizing arterio-venous malformations, and can be injected through a standard microcatheter, with flow. These hydrogel particles become fully swollen after about 15 minutes at physiological pH of about 7.4.

Example 4

Occlusion of Blood Vessels or Other Luminal Anatomical Structures

To make vessel occlusion plugs, 1.52 g (0.021 moles) acrylamide, 0.87 g (0.009 moles) sodium acrylate, 0.005 g (0.00003 moles) N,N-methylenebisacrylamide, 7.95 g water, and 4.5 g sodium chloride (<10 micron particle size) are added to an amber jar. The initiators, 53 microliters of N,N,N',N'-tetramethylethylenediamine and 65 microliters of 20% w/w ammonium persulfate in water, are added and the solution is aspirated into a 3-cc syringe. The solution is then injected into various sizes of tubing and allowed to polymerize for 2 hours. The various sizes of tubing are required to make different sizes of vessel occlusion plugs. For example, polymerization in 0.025" ID tubing results in vessel plugs with a diameter of about 0.035". Polymerization in 0.019" ID tubing results in vessel plugs with a diameter of about 0.026". The tubing is cut into 2-inch sections and dried in a vacuum oven. The dried hydrogel is removed from the tubing using a mandrel. The polymerized hydrogel is washed three times in distilled water for about 10-12 hours, about 2 hours and about 2 hours, respectively, to remove porosigen, any unreacted monomer and any unincorporated oligomer(s). The hydrogel is then cut into sections or pellets of approximately 0.500 inch in length and skewered with a platinum coil/ware assembly. These skewered hydrogel pellets are then dehydrated in ethanol and dried under vacuum at about 55 C for about 2 hours. The skewered, dried pellets are then placed in an acidification solution of 50% hydrochloric acid:50% water for about 22 hours and incubated at approximately 37 C. After the incubation, the excess hydrochloric acid solution is rinsed off of the pellets with consecutive rinses of a) 70% isopropyl alcohol:30% water for about 5 minutes, b) 100% isopropyl alcohol for about 15 minutes, c) 100% isopropyl for about 15 minutes and d) 100% isopropyl alcohol for about 15 minutes. After completion of these alcohol rinses, the treated hydrogel pellets are then dried under vacuum at about 55 C for approximately 2 hours.

The treated, dried hydrogel pellets prepared using this procedure have a diameter suitable for delivery through a 0.014 inch or 0.018 inch (ID) microcatheter filled with saline or blood. The material can be injected through the microcatheter with flow or delivered through the microcatheter attached to a detachable delivery system. If the detachable system is utilized, the hydrogel material is repositionable in and out of the microcatheter for about 5 minutes before significant swelling occurs. The material is fully swollen in about 15 minutes.

It will be appreciated that in any embodiment of the invention, the hydrogel may further include or incorporate a medicament (e.g., drug, biological, gene, gene therapy preparation, diagnostic agent, imageable contrast material, growth factor, other biological factor, peptide or other bioactive, therapeutic or diagnostic substance) to cause a desired medicament effect (a therapeutic, diagnostic, pharmacological or other physiological effect) at or near the implantation site. Examples of some of the types of medicaments that may be incorporated into the hydrogels of this invention are described in U.S. Pat. Nos. 5,891,192 (Muraysma, et al.), 5,958,428 (Bhatnagar) and 6,187,024 (Block at al.) and in PCT International Publication WO 01/03607 (Slalkeu et al.), the entireties of each such document being expressly incorporated herein by reference.

The invention has been described herein with reference to certain examples and embodiments only. No effort has been made to exhaustively describe all possible examples and embodiments of the invention. Indeed, those of skill in the art will appreciate that various additions, deletions, modifications and other changes may be made to the above-described examples and embodiments, without departing from the intended spirit and scope of the invention as recited in the following claims. It is intended that all such additions, deletions, modifications and other changes be included within the scope of the following claims.

The invention claimed is:

1. A method for implanting a hydrogel polymer at an implantation site within the body of a human or animal subject, said method comprising:
   providing a hydrogel formed from one or more ethylenically unsaturated monomers at least some of which have ionizable functional groups, a crosslinker and an initiator;
   providing a catheter having a lumen, said catheter being insertable into the subject's body and advanceable to the implantation site;
   contacting the hydrogel with a treatment solution having a low pH at a predetermined temperature and for a predetermined time so that the protonation state of the hydrogel is altered in a predetermined fashion;
   drying the hydrogel to form a dried hydrogel mass;
   placing the dried hydrogel mass within a catheter lumen; and
   delivering the dried hydrogel mass out of the catheter lumen to the implantation site such that the pH present at the implantation site changes the protonation of the dried hydrogel mass such that the hydrogel expands at a predetermined rate.

2. The method of claim 1 wherein the hydrogel is contacted with a treatment solution so that the functional groups of the hydrogel become protonated and wherein the pH at the implantation site causes the hydrogel delivered thereto to deprotonate in a predetermined fashion.

3. The method of claim 1 wherein the hydrogel remains small enough to be retracted into the catheter lumen for at least about 5 minutes after first being delivered to the implantation site.

4. A method of claim 3 wherein the catheter comprises a microcatheter.

5. A method of claim 3 wherein the hydrogel remains retractable into and readvanceable out of the catheter lumen for at least about 5 minutes after first being delivered to the implantation site.

6. The method of claim 1 wherein the physiological site comprises a wound, tumor, aneurysm, blood vessel that supplies blood to a tumor, an organ, an aberrant blood vessel or vascular structure, a space located between or among tissues or anatomical structures, or a surgically created pocket or space.

7. The method of claim 1 wherein the method further comprises the step of: delivering a medicament to the implantation site.

8. The method of claim 7 wherein the medicament is combined with the hydrogel.

9. The method of claim 1 wherein porosity is imparted to the hydrogel by a porosigen.

10. The method of claim 1 wherein the hydrogel is sufficiently porous to permit cellular ingrowth.

11. The method of claim 1 wherein radiopaque material is incorporated into the hydrogel to impart radiopacity.

12. The method of claim 1 wherein the pH present at the physiological site is approximately 7.4.

13. A method for treating a disorder in a human or animal subject by introduction of a hydrogel polymer through a lumen of a catheter, said method comprising:
   forming a hydrogel polymer by combining at least an ethylenically unsaturated monomer or prepolymer having ionizable functional groups, a crosslinker, and a polymerization initiator;
   contacting the hydrogel with a treatment solution having a predetermined pH at a specific temperature and for a predetermined time so that the functional groups of the hydrogel become protonated in a predetermined fashion;
   drying the hydrogel to form a dried hydrogel mass capable of being passed through the lumen of the catheter;
   placing the dried hydrogel mass within the lumen of the catheter; and
   delivering the dried hydrogel mass, through the lumen of the catheter, to a site within the subject's body such that the pH present at the site causes the dried hydrogel mass to deprotonate such that the hydrogel expands at a predetermined rate within the site.

14. The method of claim 13 wherein the hydrogel is retractable into the lumen of the catheter for at least about 5 minutes after having been initially delivered to the site.

15. The method of claim 14 wherein the hydrogel remains retractable into and readvanceable out of the catheter lumen for at least about 5 minutes after having been initially delivered to the site.

16. The method of claim 15 wherein the catheter comprises a microcatheter.

17. The method of claim 15 wherein the method further comprises the step of: delivering a medicament to the site.

18. The method of claim 17 wherein the medicament is combined with the hydrogel.

19. The method of claim 13 wherein radiopaque material is incorporated into the hydrogel to impart radiopacity.

20. A method for treating a disorder in a human or animal subject by introduction of a hydrogel polymer through a lumen of a catheter, said method comprising:
   forming a hydrogel polymer by combining at least an ethylenically unsaturated monomer or prepolymer having ionizable functional groups, a crosslinker, a polymerization initiator, and a porosigen;
   contacting the hydrogel with a treatment solution having a predetermined pH at a specific temperature and for a predetermined time so that the functional groups of the hydrogel become protonated in a predetermined fashion;
   drying the hydrogel to form a dried hydrogel mass capable of being passed through a catheter;
   placing the dried hydrogel mass within the catheter lumen; and
   delivering the dried hydrogel mass, through the catheter, to a physiological site having a pH of approximately 7.4 which causes the dried hydrogel mass delivered thereto to deprotonate such that the hydrogel expands at a predetermined rate and wherein the hydrogel is repositionable in and out of the microcatheter for about five minutes before significant expansion occurs.

21. The method of claim 20 wherein the method further comprises the step of: delivering a medicament to the site.

22. The method of claim 21 wherein the medicament is combined with the hydrogel.

23. The method of claim 20 wherein radiopaque material is incorporated into the hydrogel to impart radiopacity.

24. The method of claim 20 further comprising the step of removing the porosigen thereby causing the hydrogel to be porous.

25. The method of claim 24 wherein the step of removing the porosigen comprises exposing the hydrogel to a solvent that dissolves the porosigen.

26. The method of claim 1 wherein said initiator is selected from the group consisting of reduction-oxidation initiator, radiation, heat, and combinations thereof.

* * * * *

UNITED STATES PATENT AND TRADEMARK OFFICE
CERTIFICATE OF CORRECTION

| | | |
|---|---|---|
| PATENT NO. | : 8,231,890 B2 | Page 1 of 1 |
| APPLICATION NO. | : 11/090806 | |
| DATED | : July 31, 2012 | |
| INVENTOR(S) | : Cruise et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1539 days.

Signed and Sealed this
Thirteenth Day of November, 2012

David J. Kappos
*Director of the United States Patent and Trademark Office*